United States Patent
Gruber

(10) Patent No.: US 9,649,376 B2
(45) Date of Patent: *May 16, 2017

(54) SELECTIVE REMOVAL OF AGE-MODIFIED CELLS FOR TREATMENT OF ATHEROSCLEROSIS

(75) Inventor: Lewis Gruber, Chicago, IL (US)

(73) Assignee: Siwa Corporation, Chicago, IL (US)

( * ) Notice: Subject to any disclaimer, the term of this patent is extended or adjusted under 35 U.S.C. 154(b) by 807 days.

This patent is subject to a terminal disclaimer.

(21) Appl. No.: 13/876,157

(22) PCT Filed: Sep. 27, 2011

(86) PCT No.: PCT/US2011/053399
§ 371 (c)(1),
(2), (4) Date: May 28, 2013

(87) PCT Pub. No.: WO2012/047629
PCT Pub. Date: Apr. 12, 2012

(65) Prior Publication Data
US 2013/0243785 A1 Sep. 19, 2013

Related U.S. Application Data

(60) Provisional application No. 61/386,932, filed on Sep. 27, 2010.

(51) Int. Cl.
| C07K 16/44 | (2006.01) |
| A61K 39/395 | (2006.01) |
| A61K 41/00 | (2006.01) |
| A61B 17/32 | (2006.01) |

(52) U.S. Cl.
CPC .. *A61K 39/3955* (2013.01); *A61B 17/320068* (2013.01); *A61K 39/39533* (2013.01); *A61K 41/0023* (2013.01); *C07K 16/44* (2013.01)

(58) Field of Classification Search
CPC .................... C07K 16/44; A61K 39/39533
See application file for complete search history.

(56) References Cited

U.S. PATENT DOCUMENTS

| 4,217,344 A | 8/1980 | Vanlerberghe et al. |
| 4,900,747 A | 2/1990 | Vlassara et al. |
| 4,911,928 A | 3/1990 | Wallach |
| 4,917,951 A | 4/1990 | Wallach |
| 5,494,791 A | 2/1996 | Cohen |
| 5,518,720 A | 5/1996 | Cohen |
| 5,601,526 A | 2/1997 | Chapelon et al. |
| 5,620,479 A | 4/1997 | Diederich |
| 5,693,762 A | 12/1997 | Queen et al. |
| 5,702,704 A | 12/1997 | Bucala |
| 5,766,590 A | 6/1998 | Founds et al. |
| 5,811,075 A | 9/1998 | Vlassara et al. |
| 5,817,771 A | 10/1998 | Bayley et al. |
| 5,984,882 A | 11/1999 | Rosenschein et al. |
| 6,067,859 A | 5/2000 | Kas et al. |
| 6,090,382 A | 7/2000 | Salfeld et al. |
| 6,176,842 B1 | 1/2001 | Tachibana et al. |
| 6,245,318 B1 | 6/2001 | Klibanov et al. |
| 6,309,355 B1 | 10/2001 | Cain et al. |
| 6,380,165 B1 | 4/2002 | Al-Abed et al. |
| 6,387,373 B1 | 5/2002 | Wright et al. |
| 6,670,136 B2 | 12/2003 | Schmidt et al. |
| 6,676,963 B1 | 1/2004 | Lanza et al. |
| 6,818,215 B2 | 11/2004 | Smith et al. |
| 6,821,274 B2 | 11/2004 | McHale et al. |
| 7,033,574 B1 | 4/2006 | Schneider et al. |
| 7,101,838 B2 | 9/2006 | Stern et al. |
| 7,256,273 B2 | 8/2007 | Basi et al. |
| 7,347,855 B2 | 3/2008 | Eshel et al. |
| 7,358,226 B2 | 4/2008 | Dayton et al. |
| 7,367,988 B1 | 5/2008 | Litovitz |
| 7,751,057 B2 | 7/2010 | Oldenburg et al. |
| 7,815,570 B2 | 10/2010 | Eshel et al. |
| 8,343,420 B2 | 1/2013 | Cioanta et al. |
| 8,398,977 B2 | 3/2013 | Bleck et al. |
| 8,721,571 B2 | 5/2014 | Gruber |
| 9,320,919 B2 | 4/2016 | Gruber |
| 2002/0193784 A1 | 12/2002 | McHale et al. |
| 2003/0073138 A1 | 4/2003 | Kientsch-Engel et al. |
| 2003/0170173 A1 | 9/2003 | Klaveness et al. |
| 2003/0229283 A1 | 12/2003 | Craig et al. |
| 2004/0039416 A1 | 2/2004 | Myhr |
| 2004/0141922 A1 | 7/2004 | Klaveness et al. |

(Continued)

FOREIGN PATENT DOCUMENTS

| AU | 2009/248945 | 5/2014 |
| CN | 201510303227.8 | 12/2016 |

(Continued)

OTHER PUBLICATIONS

DeNardo et al., Clin Cancer Res. Oct. 1, 2005;11(19 Pt 2):7087s-7092s.*
Chen et al., Free Radic Biol Med. Dec. 1995;19(6):713-724.*
Bumol, T.F. et al., "Monoclonal antibody and an antibody-toxin conjugate to a cell surface proteoglycan of melanoma cells suppress in vivo tumor growth", Proceeding of the National Academy of Science, vol. 80, pp. 529-533, (1983).
"AGEs (all species) antibody—Product Details", Antibodies Online, 4 pages, found at www.web.archive.org/web/20081229071154/http://www.antibodies-online.com/antibody/289931/AGEs+All+Species/, printed on Dec. 10, 2014.

(Continued)

*Primary Examiner* — Daniel C Gamett
(74) *Attorney, Agent, or Firm* — Evan Law Group LLC

(57) ABSTRACT

A method of treating atherosclerosis comprises removing AGE-modified cells from a patient. The AGE-modified cells include erythrocytes, intima cells, endothelial cells, smooth muscle cells, macrophages, and foam cells. A variety of techniques, such as ultrasound and binding with an anti-AGE antibody, may be used to identify and remove the AGE-modified cells.

20 Claims, No Drawings

(56) References Cited

U.S. PATENT DOCUMENTS

| | | |
|---|---|---|
| 2004/0208826 A1 | 10/2004 | Schneider et al. |
| 2004/0229830 A1 | 11/2004 | Tachibana et al. |
| 2005/0084538 A1 | 4/2005 | Dayton et al. |
| 2005/0283098 A1 | 12/2005 | Conston et al. |
| 2006/0078501 A1 | 4/2006 | Goertz et al. |
| 2006/0122543 A1 | 6/2006 | Mayer et al. |
| 2006/0188883 A1 | 8/2006 | Murray et al. |
| 2007/0059247 A1 | 3/2007 | Lindner et al. |
| 2007/0065415 A1 | 3/2007 | Kleinsek et al. |
| 2007/0083120 A1 | 4/2007 | Cain et al. |
| 2007/0128117 A1 | 6/2007 | Bettinger et al. |
| 2007/0129633 A1 | 6/2007 | Lee et al. |
| 2008/0019986 A1 | 1/2008 | Stern et al. |
| 2008/0051680 A1 | 2/2008 | Luebcke |
| 2008/0063603 A1 | 3/2008 | Schneider et al. |
| 2008/0139942 A1 | 6/2008 | Gaud et al. |
| 2008/0160506 A1 | 7/2008 | Liu et al. |
| 2009/0076390 A1 | 3/2009 | Lee et al. |
| 2009/0306552 A1 | 12/2009 | Furuzono et al. |
| 2010/0028359 A1 | 2/2010 | Gu et al. |
| 2010/0226932 A1 | 9/2010 | Smith et al. |
| 2011/0105961 A1 | 5/2011 | Gruber |
| 2012/0130287 A1 | 5/2012 | Gruber |
| 2012/0183534 A1 | 7/2012 | Gruber |
| 2013/0131006 A1 | 5/2013 | Hee et al. |
| 2014/0303526 A1 | 10/2014 | Gruber |
| 2016/0101299 A1 | 4/2016 | Gruber |
| 2016/0152697 A1 | 6/2016 | Gruber |
| 2016/0175413 A1 | 6/2016 | Gruber |

FOREIGN PATENT DOCUMENTS

| | | |
|---|---|---|
| DE | 102008009461 | 8/2009 |
| IN | 4875/KOLNP/2010 | 12/2016 |
| WO | 96/20958 | 7/1996 |
| WO | 97/49429 | 12/1997 |
| WO | 99/14587 | 3/1999 |
| WO | 99/64463 | 12/1999 |
| WO | 00/20458 | 4/2000 |
| WO | 2004/016229 | 2/2004 |
| WO | 2006/012415 | 2/2006 |
| WO | 2006/017647 | 2/2006 |
| WO | 2006/040597 | 4/2006 |
| WO | 2009/136382 | 11/2009 |
| WO | 2009/143411 | 11/2009 |
| WO | 2012/047629 | 4/2012 |
| WO | 2012/071269 | 5/2012 |
| WO | 2012/135616 | 10/2012 |
| WO | 2013/009785 | 1/2013 |
| WO | 2013/043161 | 3/2013 |
| WO | 2015/112835 | 7/2015 |
| WO | 2016/044252 | 3/2016 |
| WO | 2016/039076 | 12/2016 |

OTHER PUBLICATIONS

"Antibody Engineering", Fusion Antibodies, 2 pages, found at www.web.archive.org/web/20080628225818/http://www.fusionantibodies.com/index.cfm/area/information/page/engineering?, printed on Dec. 16, 2014.
U.S. Appl. No. 12/951,768, mailed Nov. 15, 2013, 3 pages.
WO PCT/US2012/031446, mailed Oct. 10, 2013, 6 pages.
JP 2011-511734, mailed Nov. 19, 2013, 8 pages.
CN 200980118817.6, mailed Oct. 10, 2013, 8 pages.
U.S. Appl. No. 12/951,768, mailed Dec. 20, 2013, 15 pages.
KR 10-2010-7026063, mailed Dec. 23, 2013, 7 pages.
Leinenga, G. et al., "Scanning ultrasound removes amyloid-β and restores memory in an Alzheimer's disease mouse model", Science Translational Medicine, vol. 7, issue 278, pp. 1-11, (2015).
CA 2,724,886, mailed Feb. 5, 2015, 3 pages.
KR 10-2012-7026483, mailed Feb. 27, 2015, 6 pages.
U.S. Appl. No. 12/994,421, mailed Mar. 13, 2015, 5 pages.
U.S. Appl. No. 13/332,976, mailed Mar. 13, 2015, 6 pages.
U.S. Appl. No. 12/994,421, mailed Jun. 14, 2012, 6 pages.
WO PCT/US2009/44951, mailed Jul. 21, 2009, 19 pages.
WO PCT/US2009/44951, mailed Dec. 2, 2010, 6 pages.
WO PCT/US2011/053399, mailed Apr. 26, 2012, 13 pages.
U.S. Appl. No. 12/951,768, mailed Jul. 2, 2012, 3 pages.
U.S. Appl. No. 12/951,768, mailed Mar. 30, 2012, 21 pages.
WO PCT/US2011/061387, mailed Jun. 13, 2012, 12 pages.
WO PCT/US12/31446, mailed Jun. 27, 2012, 13 pages.
CN 200980118817.6, mailed May 14, 2012, 5 pages.
EP 09 751 639.7, mailed Nov. 8, 2011, 9 pages.
EP 09 751 639.7, mailed Jun. 12, 2012, 6 pages.
U.S. Appl. No. 12/994,421, mailed Jul. 20, 2012, 3 pages.
KR 10-2012-7026063, mailed Jul. 13, 2012, 4 pages.
U.S. Appl. No. 12/994,421, mailed Sep. 10, 2012, 27 pages.
U.S. Appl. No. 12/951,768, mailed Nov. 5, 2012, 9 pages.
AU 2009248945, mailed Nov. 8, 2012, 4 pages.
IL 209513, mailed Aug. 20, 2012, 4 pages.
EP 09 751 639.7, mailed Jan. 3, 2013, 6 pages.
U.S. Appl. No. 12/994,421, mailed Feb. 26, 2013, 10 pages.
RU 2010152693, mailed Dec. 25, 2012, 5 pages.
U.S. Appl. No. 12/951,768, mailed Mar. 21, 2013, 3 pages.
CN 200980118817.6, mailed Feb. 28, 2013, 5 pages.
KR 10-2010-7026063, mailed Feb. 28, 2013, 10 pages.
U.S. Appl. No. 12/951,768, mailed Mar. 27, 2013, 3 pages.
AU 2009248945, mailed Apr. 15, 2013, 3 pages.
Peppa, M. et al., "Glucose, advanced glycation end products, and diabetes complications: What is new and what works", Clinical Diabetes, vol. 21, No. 4, pp. 186-187, (2003).
Lv, Y. et al., "Low-intensity ultrasound combined with 5-aminolevulinic acid administration in the treatment of human tongue squamous carcinoma", Cellular Physiology and Biochemistry, vol. 30, pp. 321-333, (2012).
Campisi, J. et al., "Cellular senescence: when bad things happen to good cells", Nature Reviews: Molecular Cell Biology, vol. 8, pp. 729-749, (2007).
"ALSUntangled No. 23: The Rife Machine and retroviruses", Amyotrophic Lateral Sclerosis and Frontotemporal Degeneration, vol. 15, pp. 157-159, (2014).
Roylance, D., "Mechanical properties of materials", pp. 1-128, (2008), available at www.web.mit.edu/course/3/3.225/book.pdf.
Vidarsson, G. et al., "IgG subclasses and allotypes: from structure to effector functions", Frontiers in Immunology, vol. 5, article 520, pp. 1-17, (2014).
Lin, H-T. et al., "Stem cell therapy: an exercise in patience and prudence", Philosophical Transactions of the Royal Society B: Biological Sciences 368, (2013).
U.S. Appl. No. 14/994,421, mailed May 21, 2013, 3 pages.
RU 2010152693, mailed Apr. 23, 2013, 9 pages.
WO PCT/US2011/061387, mailed May 30, 2013, 7 pages.
IL 209513, mailed May 22, 2013, 3 pages.
U.S. Appl. No. 13/332,976, mailed Sep. 3, 2014, 6 pages.
U.S. Appl. No. 14/247,081, mailed Sep. 9, 2014, 30 pages.
Meuter, A. et al., "Markers of cellular senescence are elevated in murine blastocysts cultured in vitro: molecular consequences of culture in atmospheric oxygen", Journal of Assisted Reproduction and Genetics, vol. 31, issue 10, pp. 1259-1267, (2014).
Freund, A. et al., "Inflammatory networks during cellular senescence: causes and consequences", Trends in Molecular Medicine, vol. 16, No. 5, pp. 238-246, (2010).
Hadrabová, J. et al., "Chicken immunoglobulins for prophylaxis: Effect of inhaled antibodies on inflammatory parameters in rat airways", Journal of Applied Biomedicine, 4 pages, Available online May 5, 2014.
Ferraccioli, G. et al., "Interleukin-1β and Interleukin-6 in arthritis animal models: Roles in the early phase of transition from acute to chronic inflammation and relevance for human rheumatoid arthritis", Molecular Medicine, vol. 16, issue 11-12, pp. 552-557, (2010).
Zhao, Y. et al., "The bovine antibody repertoire", Developmental & Comparative Immunology, vol. 30, issues 1-2, pp. 175-186, (2006).
Wagner, B. et al., "The complete map of the Ig heavy chain constant gene region reveals evidence for seven IgG isotypes and for IgD in the horse", Journal of Immunology, vol. 173, No. 5, pp. 3230-3242, (2004).

(56) References Cited

OTHER PUBLICATIONS

Strietzel, C.J. et al., "In vitro functional characterization of feline IgGs", Veterinary Immunology and Immunopathology, vol. 158, issues 3-4, pp. 214-223, (2014).
Patel, M. et al., "Sequence of the dog immunoglobulin alpha and epsilon constant region genes", Immunogenetics, vol. 41, issue 5, pp. 282-286, (1995).
Maass, D.R. et al., "Alpaca (*Lama pacos*) as a convenient source of recombinant camelid heavy chain antibodies (VHHs)", Journal of Immunology Methods, vol. 324, issues 1-2, pp. 13-25, (2007).
European Search Report dated Sep. 12, 2014 for EP application No. EP14170802.4-1408.
Fessler, J. et al., "Senescent T cells promote bone loss in rheumatoid arthritis", Abstracts of the American College of Rheumatology/Association of Rheumatology Health Professionals, Annual Scientific Meeting, Washington DC, Nov. 9-14, 2012, Arthritis & Rheumatism, vol. 64, supplement 10, p. 2312, (2012) found at http://blackwellpublishing.com/acrmeeting/abstract.asp?MeetingID=789&id=103040.
Weyand, C.M. et al., Abstract of "T-cell aging in rheumatoid arthritis", Current Opinion in Rheumatology, vol. 26, No. 1, pp. 93-100, (2014) found at http://www.ncbi.nlm.nih.gov/m/pubmed/24296720/.
Dvergsten, J. et al., "Prevalence of functionally active, senescent T cells in juvenile idiopathic arthritis", Abstracts of the American College of Rheumatology/Association of Rheumatology Health Professionals, Annual Scientific Meeting, Philadelphia, Oct. 16-21, 2009, Arthritis & Rheumatism, vol. 60, supplemental 10, p. 1313, (2009), found at http://blackwellpublishing.com/acrmeeting/abstract.asp?MeetingID=761&id=80937.
Definition of "Dissociation constant" printed from Wikipedia, the free encyclopedia on Sep. 17, 2014 found at http://en.wikipedia.org/wiki/Dissociation_constant.
Sigma-Aldrich product specification of "Nα,Nα-Bis(carboxymethyl)-L-lysine trifluoroacetate salt ≥95% (TLC)", found at http://sigmaaldrich.com/catalog/product/sigma/c3205?lang=en&region=US, printed on Sep. 17, 2014.
"Pulmatrix demonstrates iSPERSE capabilities for inhaled dry powder delivery of antibiotics and antibodies", data presented at Respiratory Drug Delivery 2012, 3 pages, printed on Sep. 4, 2014, found at http://businesswire.com/news/home/20120515005279/en/Pulmatrix-Demonstrates-iSPERSE-Capabilities-Inhaled-Dry-Powder#.VEgU4hauNbs.
Chan, A.C. et al., "Therapeutic antibodies for autoimmunity and inflammation", Nature Reviews Immunology, vol. 10, pp. 301-316, (2010).
Pradat, P.F. et al., "Abnormalities of satellite cells function in amyotrophic lateral sclerosis", Amyotrophic Lateral Sclerosis, vol. 12, No. 4, pp. 264-271, (2011).
Tchkonia, T. et al., "Cellular senescence and the senescent secretory phenotype: therapeutic opportunities", The Journal of Clinical Investigation, vol. 123, No. 3, pp. 966-972, (2013).
Kitada, K. et al., "Aldosterone induces p21-regulated apoptosis via increased synthesis and secretion of tumour necrosis factor-α in human proximal tubular cells", Clinical and Experimantal Pharmacology and Physiology, vol. 39, No. 10, pp. 858-863, (2012).
Definition of "TNF inhibitor", printed from Wikipedia, the free encyclopedia on Oct. 4, 2014, 4 pages, found at http://en.wikipedia.org/wiki/TNF_inhibitor?oldid=628250399.
Definition of "Etanercept", printed from Wikipedia, the free encyclopedia on Aug. 24, 2014, 6 pages, found at http://en.wikipedia.org/wiki/Etanercept?oldid=622648157.
AbbVie, Inc., "Humira adalimumab: Learn about Humira", found at https://www.humira.com/rheumatoid-arthritis, 7 pages, printed on Aug. 11, 2014.
AbbVie, Inc., "Medication Guide for Humira", found at https://www.humira.com/rheumatoid-arthritis, 9 pages, printed on Aug. 11, 2014.
AbbVie, Inc., "Humira: A biologic that targets and helps block TNF-alpha", found at https://www.humira.com/rheumatoid-arthritis/how-humira-works-for-ra, 8 pages, printed on Aug. 11, 2014.
AbbVie, Inc., "How Humira (adalimumab) works video transcript", found at https://www.humira.com/rheumatoid-arthritis/how-humira-works-video-transcript, 5 pages, printed on Aug. 11, 2014.
AbbVie, Inc., "Humira and methotrexate—a combination that has demonstrated results", found at https://www.humira.com/rheumatoid-arthritis/humira-and-methotrexate, 7 pages, printed on Aug. 11, 2014.
Madhur, M.S. et al., "Senescent T cells and hypertension: New ideas about old cells", Hypertension, vol. 62, pp. 13-15, (2013).
James, P.E. et al., "Vasorelaxation by red blood cells and impairment in diabetes: Reduced nitric oxide and oxygen delivery by glycated hemoglobin", Circulation Research, vol. 94, pp. 976-983, (2004).
EP 14170802.4, mailed Sep. 12, 2014, 6 pages.
CN 200980118817.6, mailed Oct. 8, 2014, 7 pages.
U.S. Appl. No. 13/332,976, mailed Nov. 18, 2014, 51 pages.
U.S. Appl. No. 12/994,421, mailed Nov. 18, 2014, 34 pages.
Hargreaves, R.E.G. et al., "Selective depletion of activated T cells: the CD40L-specific antibody experience", TRENDS in Molecular Medicine, vol. 10, No. 3, pp. 130-135, (2004).
Wautier, J-L. et al., "Protein Glycation: A firm link to endothelial cell dysfunction", Circulation Research, Journal of the American Heart Association, vol. 95, pp. 233-238, (2004).
U.S. Appl. No. 14/247,081, mailed Jan. 13, 2015, 3 pages.
U.S. Appl. No. 14/247,081, mailed Feb. 2, 2015, 5 pages.
RU 2010152693, mailed Dec. 16, 2014, 10 pages.
U.S. Appl. No. 12/994,421, mailed Mar. 27, 2015, 44 pages.
U.S. Appl. No. 13/332,976, mailed Apr. 1, 2015, 25 pages.
CN 200980118817.6, mailed Mar. 26, 2015, 4 pages.
International Search Report dated Jul. 21, 2009 for PCT application No. PCT/US2009/44951.
Lindsey, J.B. et al., "Receptor for advanced glycation end-products (RAGE) and soluble RAGE (sRAGE): Cardiovascular implications", Diabetes Vascular Disease Research, vol. 6, No. 1, pp. 7-14, (2009).
Ando, K. et al., "Membrane proteins of human erythrocytes are modified by advanced glycation end products during aging in the circulation", Biochemical and Biophysical Research Communications, vol. 258, pp. 123-127, (1999).
Jandeleit-Dahm, K. et al., "The AGE/RAGE axis in diabetes-accelerated atherosclerosis", Clinical and Experimental Pharmacology and Physiology, vol. 35, pp. 329-334, (2008).
Sakata, N. et al., "Immunohistochemical localization of different epitopes of advanced glycation end products in human atherosclerotic lesions", Atherosclerosis, vol. 141, pp. 61-75, (1998).
Karachalias, N. et al., "Accumulation of fructosyl-lysine and advanced glycation end products in the kidney, retina and peripheral nerve of streptozotocin-induced diabetic rats", Biochemical Society Transactions, vol. 31, pp. 1423-1425, (2003).
Aroian, R. et al., "Pore-forming toxins and cellular non-immune defenses (CNIDs)", Current Opinion in Microbiology, vol. 10, pp. 57-61, (2007).
Dobson, J., "A twist on tumour targeting", Nature Materials, vol. 9, pp. 95-96, (2010).
Gutensohn, K. et al., "Extracorporeal plateletpheresis induces the interaction of activated platelets with white blood cells", Vox Sanguinis, vol. 78, No. 2, pp. 101-105, (2000).
Horiuchi, S. et al., "Immunochemical approach to characterize advanced glycation end products of the maillard reaction", The Journal of Biological Chemistry, vol. 266, No. 12, pp. 7329-7332, (1991).
Soetanto, K. et al., "Fundamental examination of cattle red blood cells damage with ultrasound exposure microscopic system (UEMS)", Japanese Journal of Applied Physics, vol. 37, part 1, No. 5B, pp. 3070-3073, (1998).
Harja, E. et al., "Vascular and inflammatory stresses mediate atherosclerosis via RAGE and its ligands in apoE-/- mice", The Journal of Clinical Investigation, vol. 118, No. 1, pp. 183-194, (2008).

(56) References Cited

OTHER PUBLICATIONS

Carstensen, E.L. et al., "Lysis of erythrocytes by exposure to cw ultrasound", Ultrasound in Medicine and Biology, vol. 19, No. 2, pp. 147-165, (1993).
Miller, M.W. et al., "Comparative sensitivity of human erythrocytes and lymphocytes to sonolysis by 1-MHz ultrasound", Ultrasound in Medicine and Biology, vol. 23, No. 4, pp. 635-638, (1997).
Iwata, H. et al., "Effect of carbonyl compounds on red blood cells deformability", Biochemical and Biophysical Research Communications vol. 321, pp. 700-706, (2004).
Schmitt, A. et al., "The binding of advanced glycation end products to cell surfaces can be measured using bead-reconstituted cellular membrane proteins", Biochimica et Biophysica Acta, vol. 1768, pp. 1389-1399, (2007).
Self-Medlin, Y. et al., "Glucose promotes membrane cholesterol crystalline domain formation by lipid peroxidation", Biochimica et Biophysica Acta, vol. 1788, pp. 1398-1403, (2009).
Singh, N. et al., "The PPAR-y activator, rosiglitazone, inhibits actin polymerisation in monocytes: involvement of Akt and intracellular calcium", Biochemical and Biophysical Research Communications, vol. 333, pp. 455-462, (2005).
Li, Y-M. et al., "Effects of high glucose on mesenchymal stem cell proliferation and differentiation", Biochemical and Biophysical Research Communications, vol. 363, pp. 209-215, (2007).
Takata, K. et al., "Endocytic uptake of nonenzymatically glycosylated proteins is mediated by a scavenger receptor for aldehyde-modified proteins", The Journal of Biological Chemistry, vol. 263, No. 29, pp. 14819-14825, (1988).
Mi, Y. et al., "Apoptosis in leukemia cells is accompanied by alterations in the levels and localization of nucleolin", Journal of Biological Chemistry, vol. 278, pp. 8572-8579, (2003).
Christian, S. et al., "Nucleolin expressed at the cell surface is a marker of endothelial cells in angiogenic blood vessels", Journal of Cell Biology, vol. 163, No. 4, pp. 871-878, (2003).
Loo, T.W. et al., "Identification of residues in the drug translocation pathway of the human multidrug resistance P-glycoprotein by arginine mutagenesis", Journal of Biological Chemistry, vol. 284, No. 36, pp. 24074-24087, (2009).
Brundin, P. et al., "Prion-like transmission of protein aggregates in neurodegenerative diseases", Nature Reviews Molecular Cell Biology, vol. 11, No. 4, pp. 301-307, (2010).
Perez, C. et al., "Translational control of the abundance of cytoplasmic poly(A) binding protein in human cytomegalovirus-infected cells", Journal of Virology, vol. 85, No. 1, pp. 156-164, (2011).
Persson, J. et al., "Interleukin-Ibeta and tumour necrosis factor-alpha impede neutral lipid turnover in macrophage-derived foam cells", BMC Immunology, vol. 9, No. 70, pp. 1-11, (2008).
Vergne, I. et al., "Cell biology of mycobacterium tubercolosis phagosome", Annu. Rev. Cell Dev. Biology, vol. 20, pp. 367-394, (2004).
Moskowitz, S.M. et al., "The role of *Pseudomonas* lipopolysaccharide in cystic fibrosis airway Infection", Subcell Biochemistry, vol. 53, pp. 241-253, (2010).
Hall-Stoodley, L. et al., "Direct detection of bacterial biofilms on the middle-ear mucosa of children with chronic otitis media", JAMA, vol. 296, No. 2, pp. 202-211, (2006).
Franke-Fayard, B. et al., "Sequestration and tissue accumulation of human malaria parasites: Can we learn anything from rodent models of malaria?", PLoS Pathogens, vol. 6, issue 9, pp. 1-10, e1001032, (2010).
Zhang, S. et al., "Delineation of diverse macrophage activation programs in response to intracellular parasites and cytokines", PLoS Neglected Tropical Diseases, vol. 4, No. 3, e648 (2010).
Ma, Y. et al., "NS3 helicase domains involved in infectious intracellular hepatitis C virus particle assembly", Journal of Virology, vol. 82, No. 15, pp. 7624-7639, (2008).
Korant, B.D. et al., "Inhibition by zinc of rhinovirus protein cleavage: interaction of zinc with capsid polypeptides", Journal of Virology, vol. 18, No. 1, pp. 298-306, (1976).

Ameli, S. et al., "Effect of immunization with homologous LDL and oxidized LDL on early atherosclerosis in hypercholesterolemic rabbits", Arterioscerosis, Thrombosis, and Vascular Biology, vol. 16, pp. 1074-1079, (1996).
Nilsson, J. et al., "Inflammation and immunity in diabetic vascular complications", Current Opinion in Lipidology, vol. 19, issue 5, pp. 519-524, (2008).
Schiopu, A. et al., "Recombinant antibodies to an oxidized low-density lipoprotein epitope induce rapid regression of atherosclerosis in apobec-1$^{-/-}$/low-density lipoprotein receptor$^{-/-}$mice", Journal of the American College of Cardiology, vol. 50, No. 24, pp. 2313-2318, (2007).
Schiopu, A. et al., "Recombinant human antibodies against aldehyde-modified apolipoprotein B-100 peptide sequences inhibit atherosclerosis", Circulation, vol. 110, pp. 2047-2052, (2004).
Bassirat, M. et al., "Short- and long-term modulation of microvascular responses in streptozotocin-induced diabetic rats by glycosylated products", Journal of Diabetes and its Complications, vol. 24, pp. 64-72, (2010).
Ge, J. et al., "Advanced glycosylation end products might promote atherosclerosis through inducing the immune maturation of dendritic cells", Arteriosclerosis, Thrombosis, and Vascular Biology, vol. 25, pp. 2157-2163, (2005).
Gugliucci, A. et al., "Circulating advanced glycation peptides in streptozotocin-induced diabetic rats: evidence for preferential modification of IgG light chains", Life Sciences, vol. 62, No. 23, pp. 2141-2150, (1998).
Pullerits, R. et al., "Synovial fluid expression of autoantibodies specific for RAGE relates to less erosive course of rheumatoid arthritis", Rheumatology, vol. 46, pp. 1367-1371, (2007).
Bro, S. et al., "A neutralizing antibody against receptor for advanced glycation end products (RAGE) reduces atherosclerosis in uremic mice", Atherosclerosis, vol. 201, pp. 274-280, (2008).
Turk, Z. et al., "Detection of autoantibodies against advanced glycation endproducts and AGE-immune complexes in serum of patients with diabetes mellitus", Clinica Chimica Acta, vol. 303, pp. 105-115, (2001).
Li, M. et al., "Glycan changes: cancer metastasis and anti-cancer vaccines", Journal of Biosciences, vol. 35, No. 4, pp. 665-673, (2010).
Kyte, J.A. et al., "Third international conference on cancer vaccines/adjuvants/delivery for the next decade (CVADD 2009)", Expert Reviews Vaccines, vol. 9, No. 2, pp. 119-123, (2010).
Akbulut, H. et al., "Chemotherapy targeted to cancer tissue potentiates antigen-specific immune response induced by vaccine for in vivo antigen loading and activation of dendritic cells", Molecular Therapy, vol. 16, No. 10, pp. 1753-1760, (2008).
Li, Y.M. et al., "Glycation products in aged thioglycollate medium enhance the elicitation of peritoneal macrophages", Jounal of Immunological Methods, vol. 201, issue 2, pp. 183-188, (1997).
Poggioli, S. et al., "Age-related increase of protein glycation in peripheral blood lymphocytes is restricted to preferential target proteins", Experimental Gerontology, vol. 37, issue 10-11, pp. 1207-1215, (2002).
Poggioli, S. et al., "Evidence of preferential protein targets for age-related modifications in peripheral blood lymphocytes", Annals of the New York Academy of Sciences, vol. 1019, issue 1, pp. 211-214, (2004).
Dominaitiene, R. et al., "Effects of differently oxidized LDL on the expression of pro-inflammatory molecules in human monocytes in vitro", In Vitro and Molecular Toxicology, vol. 14, No. 2, pp. 83-97, (2001).
Jiang, Z-H. et al., "Synthetic vaccines: the role of adjuvants in immune targeting", Current Medicinal Chemistry, vol. 10, No. 15, pp. 1423-1439, (2003).
Buskas, T. et al., "Immunotherapy for cancer: Synthetic carbohydrate-based vaccines", Chemical Communications, Issue 36, pp. 5335-5349, (2009).
Cohen, M.P. et al., "Amelioration of diabetic nephropathy by treatment with monoclonal antibodies against glycated albumin", Kidney International, vol. 45, pp. 1673-1679, (1994).

(56) References Cited

OTHER PUBLICATIONS

Davis, P.J. et al., "How can thermal processing modify the antigenicity of proteins?", Allergy, vol. 56, supplemental 67, pp. 56-60, (2001).
Koga, M. et al. "Clinical impact of glycated albumin as another glycemic control marker", Endocrine Journal, vol. 57, No. 9, pp. 751-762, (2010).
Shcheglova, T. et al., "Reactive immunization suppresses advanced glycation and mitigates diabetic nephropathy", Journal of the American Society of Nephrology, vol. 20, No. 5, pp. 1012-1019, (2009).
Virella, G. et al., "Autoimmune response to advanced glycosylation end-products of human LDL", Journal of Lipid Research, vol. 44, pp. 487-493, (2003).
Ihssen, J. et al., "Production of glycoprotein vaccines in *Escherichia coli*", Microbial Cell Factories, vol. 9, No. 61, pp. 1-13, (2010).
Habets, K.L.L. et al., "Vaccination using oxidized low-density lipoprotein-pulsed dendritic cells reduces atherosclerosis in LDL receptor-deficient mice", Cardiovascular Research, vol. 85, pp. 622-630, (2010).
Mironova, R. et al., "Glycation and post-translational processing of human interferon-y expressed in *Escherichia coli*", The Journal of Biological Chemistry, vol. 278, No. 51, pp. 51068-51074, (2003).
Vogel, F.R. et al., "A compendium of vaccine adjuvants and excipients", Pharmaceutical Biotechnology, vol. 6, pp. 141-228, (1995).
Monograph series, World Health Organization, "Methods of Vaccine Production", part 4, chapters 18-29, pp. 189-267, (1973).
Cohen, M.P. et al., "Prevention of diabetic nephropathy in db/db mice with glycated albumin antagonists: A novel treatment strategy", The Journal of Clinical Investigation, vol. 95, pp. 2338-2345, (1995).
Naka, Y. et al., "RAGE Axis, Animal models and novel insights into the vascular complications of diabetes", Arteriosclerosis, Thrombosis, and Vascular Biology, vol. 24, pp. 1342-1349, (2004).
European Search Report dated Nov. 8, 2011 for PCT application No. PCT/US2009/044951.
Bierhaus, A. et al., "AGEs and their interaction with AGE-receptors in vascular disease and diabetes mellitus. I. the AGE concept", Cardiovascular Research, vol. 37, No. 3, pp. 586-600, (1998).
Murphy, J.F. "Trends in cancer immunotherapy", Clinical Medicine Insights: Oncology, vol. 4, pp. 67-80, (2010).
Beier, K.C., "Master switches of T-cell activation and differentiation", European Respiratory Journal, vol. 29, pp. 804-812, (2007).
Schmidlin, H., "New insights in the regulation of human B cell differentiation", Trends in Immunology, vol. 30, No. 6, pp. 277-285, (2009).
Coler, R.N. et al., "Development and characterization of synthetic glucopyranosyl lipid adjuvant system as a vaccine adjuvant", PLoS One, vol. 6, No. 1, e16333, pp. 1-12, (2011).
Cheadle, E.J., "Bugs as drugs for cancer", Immunology, vol. 107, pp. 10-19, (2002).
The Pink Book, Epidemiology and Prevention of vaccine preventable diseases, 11th Ed., pp. B7-B13, (2009), Found at www.cdc.gov/vaccines/pubs/pinkbook/downloads/appendices/b/excipient-table-1.pdf.
The Pink Book, Epidemiology and Prevention of vaccine preventable diseases, 11th Ed., 4 pages, (2009), Found at www.cdc.gov/vaccines/pubs/pinkbook/downloads/appendices/b/excipient-table-2.pdf.
Book Reviews, International Microbiology, vol. 7, pp. 291-295, (2004).
"Glycation: How eating sugar causes wrinkles", www.brighthub.com/health/diet-nutrition/artictes/18410.aspx, 1 page, published Oct. 8, 2009.
Ellis, G., "The myth of the glycemic index and its child: good carbs—bad carbs", Targeted Body Systems, www.targetedbodysystems.com/tag/low-carb-diet-plans/, pp. 1-5, published Feb. 16, 2009.
"Diabetic glycation and inflammation—what diabetes does to your coronary arteries", www.rebelheartsurgeon-antioxidants.net/diabetic-glycation.html, pp. 1-9, downloaded Aug. 17, 2010.
Dziarski, R., "Cell-bound albumin is the 70-kDa peptidoglycan-, lipopolysaccharide-, and lipoteichoic acid-binding protein on lymphocytes and macrophages", The Journal of Biological Chemistry, vol. 269, No. 32, pp. 20431-20436, (1994).
Peters Jr. T.,"5-Metabolism: Albumin in the body", All About Albumin Biochemistry, Genetics, and Medical Applications, Chapter 5, pp. 188-250, (1995).
Vlassara, H. et al., "High-affinity-receptor-mediated uptake and degradation of glucose-modified proteins: A potential mechanism for the removal of senescent macromolecules", Proceeding of the National Academy of Science, USA, Biochemistry, vol. 82, pp. 5588-5592, (1985).
Wade, N., "Purging cells in mice is found to combat aging ills", New York Times, found at NYTimes.com, pp. 1-3, (2011).
Roll, P. et al., "Anti-CD20 therapy in patients with rheumatoid arthritis", Arthritis & Rheumatism, vol. 58, No. 6, pp. 1566-1575, (2008).
Kajstura J. et al., "Myocyte turnover in the aging human heart", Circulation Research, vol. 107, pp. 1374-1386, (2010).
Baker, D.J. et al., "Clearance of p16Ink4a-positive senescent cells delays ageing-associated disorders", Nature, vol. 479, pp. 232-236, (2011).
Breyer, V. et al., "Intracellular glycation of nuclear DNA, mitochondrial DNA, and cytosolic proteins during senescence-like growth arrest", DNA Cell Biology, vol. 30, No. 9, pp. 681-689, (2011).
Ravelojaona, V. et al., "Expression of senescence-associated beta-galactosidase (SA-beta-Gal) by human skin fibroblasts, effect of advanced glycation end-products and fucose or rhamnose-rich polysaccharides", Archives of Gerontology and Geriatrics, vol. 48, issue 2, pp. 151-154, (2009).
International Search Report dated Apr. 26, 2012 for PCT application No. PCT/US2011/053399.
International Search Report dated Jun. 13, 2012 for PCT application No. PCT/US2011/061387.
Wautier, J.-L. et al., "Advanced glycation end products (AGEs) on the surface of diabetic erythrocytes bind to the vessel wall via a specific receptor inducing oxidant stress in the vasculature: A link between surface-associated AGEs and diabetic complications", Proc. Natl. Acad. Sci. USA, vol. 91, No. 16, pp. 7742-7746, (1994).
Siegel, R. J. et al., "Ultrasonic plaque ablation: A new method for recanalization of partially or totally occluded arteries", Circulation, vol. 78, No. 6, pp. 1443-1448, (1988).
International Search Report dated Jun. 27, 2012 for PCT application No. PCT/US2012/031446.
Immuno, Catalog No. 637061, 637062, "Mouse, anti-age (advanced glycation end products), monoclonal antibody", http://www.mpbio.com/detailed_info.php?family_key=0863706, 2 pages, accessed Jul. 26, 2012.
Ahmed, E. K. et al., "Protein modification and replicative senescence of WI-38 human embryonic fibroblasts", Aging Cell, vol. 9, pp. 252-272, (2010).
Vlassara, H. et al, "Advanced glycosylation endproducts on erythrocyte cell surface induce receptor-mediated phagocytosis by macrophages", J. Exp. Med., The Rockefeller University Press, vol. 166, pp. 539-549, (1987).
Yang, Z. et al., "Two novel rat liver membrane proteins that bind advanced glycosylation endproducts: Relationship to macrophage receptor for glucose-modified proteins", J. Exp. Med., The Rockefeller University Press, vol. 174, pp. 515-524, (1991).
Vlassara, H. et al, "Advanced glycation endproducts promote adhesion molecule (VCAM-1, ICAM-1) expression and atheroma formation in normal rabbits", Molecular Medicine, vol. 1, No. 4, pp. 447-456, (1995).
Vaysse, J. et al., "Adhesion and erthrophagocytosis of human senescent erthrocytes by autologous monocytes and their inhibition by β-galactosyl derivatives", Proc. Natl. Acad. Sci. USA, Cell Biology, vol. 83, pp. 1339-1343, (1986).

(56) References Cited

OTHER PUBLICATIONS

Li, Y. M. et al., "Prevention of cardiovascular and renal pathology of aging by the advanced glycation inhibitor aminoguanidine", Proc. Natl. Acad. Sci. USA, Medical Sciences, vol. 93, pp. 3902-3907, (1996).
Manesso, E. et al., "Dynamics of β-cell turnover: evidence for β-cell turnover and regeneration from sources of β-cells other than β-cell replication in the HIP rat", American Journal of Physiology—Endocrinology and Metabolism, vol. 297, pp. E323-E330, (2009).
Stepanov, A.V. et al., "Design of targeted B cell killing agents", PLoS ONE, vol. 6, issue 6, e20991, pp. 1-10, (2011).
Fact Sheet, "Targeted Cancer Therapies", www.cancer.gov/cancertopics/factsheet/Therapy/Fs7_49.pdf, pp. 1-8, (2012).
Kay, M.M. "Generation of senescent cell antigen on old cells initiates IgG binding to a neoantigen", Cellular and Molecular Biology (Noisy-le-Grand, France), vol. 39, No. 2, pp. 131-153, (1993), Abstract Only.
Cirocchi, R. et al., "Meta-analysis of thyroidectomy with ultrasonic dissector versus conventional clamp and tie", World Journal of Surgical Oncology, vol. 8, No. 112, pp. 1-7, (2010).
Lingeman, J.E. et al., "Current perspective on adverse effects in shock wave lithotripsy", White Paper, American Urological Association Education and Research, found at www.auanet.org/content/guidelines-and-quality-care/clinical-guidelines/main-reports/whitepaper.pdf, 17 pages, (2009).
De Groot, K. et al., "Vascular endothelial damage and repair in antineutrophil cytoplasmic antibody—associated vasculitis", Arthristis & Rheumatism, vol. 56, No. 11, pp. 3847-3853, (2007).
Imani, F. et al., "Advanced glycosylation endproduct-specific receptors on human and rat t-lymphocytes mediate synthesis of interferon γ: role in tissue remodeling", J. Exp. Med., vol. 178, pp. 2165-2172, (1993).
Kirstein, M. et al., "Receptor-specific induction of insulin-like growth factor I in human monocytes by advanced glycosylation end product-modified proteins", J. Clin. Invest., vol. 90, pp. 439-446, (1992).
Le Grand, F. et al., "Skeletal muscle satellite cells and adult myogenesis", Curr. Opin. Cell Biology, vol. 19, No. 6, pp. 628-633, (2007).
Sasaki, M. et al., "Mesenchymal stem cells are recruited into wounded skin and contribute to wound repair by transdifferentiation into multiple skin cell type", The Journal of Immunology, vol. 180, pp. 2581-2587, (2008).
Misur, I. et al., "Advanced glycation endproducts in peripheral nerve in type 2 diabetes with neuropathy", Acta Diabetol, vol. 41, pp. 158-166, (2004).
Saltykov, B.B., "Mechanisms of development of diabetic macroangiopathy", Arkh Patol., vol. 63, No. 2, pp. 21-26, (2001), Abstract Only.
Grossin, N. et al., "Red blood cell adhesion in diabetes mellitus is mediated by advanced glycation end product receptor and is modulated by nitric oxide", Biorheology, vol. 46, No. 1, pp. 63-72, (2009).
Liang, Y. et al., "Rituximab for children with immune thrombocytopenia: A systematic review", PLoS ONE, vol. 7, issue 1, pp. 1-11, (2012).
Fehrenbach, H. et al., "Up-regulated expression of the receptor for advanced glycation end products in cultured rat hepatic stellate cells during transdifferentiation to myofibroblasts", Hepatology, vol. 34, No. 5, pp. 943-952, (2001).
U.S. Appl. No. 13/332,976, mailed Apr. 23, 2015, 3 pages.
U.S. Appl. No. 13/332,976, mailed May 1, 2015, 3 pages.
KR 10-2013-7028228, mailed Apr. 27, 2015, 4 pages.
U.S. Appl. No. 14/247,081, mailed May 6, 2015, 29 pages.
KR 10-2015-7007520, mailed Apr. 20, 2015, 7 pages.
U.S. Appl. No. 13/332,976, mailed Jun. 11, 2015, 18 pages.
Agostini, A. et al., "Targeted cargo delivery in senescent cells using capped mesoporous silica nanoparticles", Angewandte Chemie International Edition, vol. 51, pp. 10556-10560, (2012).
Larson, R.A. et al., "Tumor lysis syndrome: Definition, pathogenesis, clinical manifestations, etiology and risk factors", found at www.uptodate.com/contents/tumor-lysis-syndrome-definition-pathogenesis-clinical-manifestations-etiology-and-risk-factors?detectedLanguage=en&source=search_result&search=tumor+lysis+syndrome&selectedTitle=2~69&provider=noProvider, pp. 1-4, printed on Jun. 11, 2013.
Hansel, T.T. et al., "The safety and side effects of monoclonal antibodies", Nature Reviews, vol. 9, pp. 325-337, (2010).
Nass, N. et al., "Advanced glycation end products, diabetes and ageing", Zeitschrift fur Gerontologie und Geriatrie, vol. 40, issue 5, pp. 349-356, (2007).
U.S. Appl. No. 12/994,421, mailed Jul. 18, 2013, 3 pages.
EP 09751639.7, mailed Jul. 26, 2013, 5 pages.
WO 11776932.3, mailed Apr. 2, 2013, 7 pages.
MX 2010/012473, mailed Jul. 16, 2013, 4 pages.
U.S. Appl. No. 12/951,768, mailed Jul. 29, 2013, 14 pages.
KR 10-2012-7026063, mailed Sep. 30, 2013, 5 pages.
Shibayama, R. et al., "Autoantibody against N(epsilon)-(carboxymethyl)lysine: an advanced glycation end product of the Maillard reaction", Diabetes, vol. 49, No. 9, pp. 1842-1849, (1999).
Waldmann, T.A., "Immunotherapy:past, present and future", Nature Medicine, vol. 9, No. 3, pp. 269-277, (2003).
Okamoto, T. et al., "Advanced glycation end products induce angiogenesis in vivo", Microvascular Research, vol. 63, pp. 186-195, (2002).
Nagai, R. et al., "Application of monoclonal antibody libraries for the measurement of glycation adducts", Biochemical Society Transactions, vol. 31, part 6, pp. 1438-1440, (2003).
KR 10-2013-7028228, mailed Jun. 22, 2014, 8 pages.
KR 10-2010-7026063, mailed Jul. 29, 2014, 3 pages.
KR 10-2012-7026483, mailed Jun. 29, 2014, 9 pages.
EP 09751639.7, mailed Jan. 23, 2014, 6 pages.
AU 2009248945, mailed Feb. 4, 2014, 3 pages.
MX 2010/012473, mailed Mar. 18, 2014, 11 pages.
CN 200980118817.6, mailed May 7, 2014, 5 pages.
IL 209513, mailed May 25, 2014, 3 pages.
RU 2010152693, mailed May 26, 2014, 7 pages.
MX 2010/012473, mailed Jun. 17, 2014, 3 pages.
CA 2,724,886, mailed Jun. 20, 2014, 3 pages.
Kirstein, et al., "Advanced protein glycosylation induces transendothelial human monocyte chemotaxis and secretion of platelet-derived growth factor: roll in vascular disease of diabetes and aging", PNAS, vol. 87, No. 22, pp. 9010-9014, (1990).
CA 2,724,886, mailed Sep. 8, 2015, 5 pages.
Drinda, S. et al., "Identification of the advanced glycation end products N-carboxymethyllysine in the synovial tissue of patients with rheumatoid arthritis", Annals of the Rheumatic Diseases, vol. 61, No. 6, pp. 488-492, (2002).
Ahmad, S. et al., "Preferential recognition of epitopes on AGE-IgG by the autoantibodies in rheumatoid arthritis patients", Human Immunology, vol. 74, No. 1, pp. 23-27, (2013).
Johns, L.D., "Nonthermal effects of therapeutic ultrasound: The frequency resonance hypothesis", Journal of Athletic Training, vol. 37, No. 3, pp. 293-299, (2002).
Wang, B-L. et al., "Identification of monoclonal antibody of advanced glycation end products", Chinese Journal of Arteriosclerosis, vol. 14, No. 5, pp. 409-412, (2006).
Wang, J.C. et al., "Aging and Atherosclerosis mechanisms, functional consequences, and potential therapeutics for cellular senescence", Circulation Research, vol. 111, pp. 245-259, (2012).
Minamino, T. et al., "Vascular cell senescence contribution to Atherosclerosis", Circulation Research, vol. 100, pp. 15-26, (2007).
Isoda, K. et al., "Glycated LDL increases monocyte CC chemokine receptor 2 expression and monocyte chemoattractant protein-1-mediated chemotaxis", Atherosclerosis, vol. 198, No. 2, pp. 307-312, (2008).
Roos, C.M. et al., "Chronic senolytic treatment alleviates established vasomotor dysfunction in aged or atherosclerotic mice", Aging Cell, 8 pages, (2016).

(56) References Cited

OTHER PUBLICATIONS

Hall, B.M. et al., "Aging of mice is associated with p16(Ink4a)- and β-galactosidase-positive macrophage accumulation that can be induced in young mice by senescent cells", Aging, vol. 8, No. 7, pp. 1-18, (2016).
Mera, K. et al., "An autoantibody against Nε-(carboxyethyl)lysine (CEL): Possible involvement in the removal of CEL-modified proteins by macrophages", Biochemical and Biophysical Research Communications, vol. 407, pp. 420-425, (2011).
Reddy, S. et al., "Nε-(Carboxymethyl)lysine is a dominant advanced glycation end product (AGE) antigen in tissue proteins", Biochemistry, vol. 34, pp. 10872-10878, (1995).
Katcher, H.L., "Studies that shed new light on aging", Biochemistry (Moscow), vol. 78, No. 9, pp. 1061-1070, (2013).
Naylor, R.M. et al., "Senescent Cells: A novel therapeutic target for aging and age-related diseases", Clinical Pharmacology & Therapeutics, vol. 93, No. 1, pp. 105-116, (2013).
Beaulieu, L-P. et al., "Inhibitory effect of the cree traditional medicine wiishichimanaanh (vaccinium vitis-idaea) on advanced glycation endproduct formation: identification of active principles", Phytotherapy Research, vol. 24, pp. 741-747, (2010).
Ulrich, P. et al., "Protein glycation, diabetes, and aging", Recent Progress in Hormone Research, vol. 56, pp. 1-21, (2000).
Van Heijst, J.W.J. et al., "Advanced glycation end products in human cancer tissues: detection of Nε-(carboxymethyl)lysine and argpyrimidine", Annals of the New York Academy of Sciences, vol. 1043, pp. 725-733, (2005).
Fielding, R.A. et al., "Sarcopenia: An undiagnosed condition in older adults. Current consensus definition: Prevalence, etiology, and consequences", Journal of the American Medical Directors Association, vol. 12, No. 4, pp. 249-256, (2011).
Definition of "Sarcopenia" printed from Wikipedia, the free encyclopedia on Jul. 25, 2016, 5 pages, found at http://en.wikipedia.org/wiki/Sarcopenia.
"What is Sarcopenia?", International Osteoporosis Foundation, 2 pages, found at www.iofbonehealth.org/what-sarcopenia, (2014).
"Sarcopenia with aging", Webmd, 2 pages, found at www.webmd.com/healthy-aging/sarcopenia-with-aging, (2014).
Definition of "Keyhole limpet hemocyanin", printed from Wikipedia, the free encyclopedia on Jul. 25, 2016, 4 pages, found at https://en.wikipedia.org/wiki/Keyhole_limpet_hemocyanin.
Cell Biolabs, Inc., "CML-BSA Product Data Sheet", 3 pages, found at http://www.cellbiolabs.com/sites/default/files/STA-314-cml-bsa.pdf, (2010).
Cell Biolabs, Inc., "CML (N-epsilon-(Caboxymethyl)Lysine) Assays and Reagents", 1 page, found at http://www.cellbiolabs.com/cml-assays, (2014).
Cruz-Jentoft, A.J. et al., "Sarcopenia: European consensus on definition and diagnosis", Age and Ageing, vol. 39, pp. 412-423, (2010).
Rolland, Y. et al., "Sarcopenia: Its assessment, etiology, pathogenesis, consequences and future perspectives", The Journal of Nutrition, Health & Aging, vol. 12, No. 7, pp. 433-450, (2008).
Centers for Disease Control and Prevention, "Vaccine excipient and media summary", 4 pages, found at www.cdc.gov/vaccines/pubs/pinkbook/downloads/appendices/B/excipient-table-2.pdf?utm_content=buffer4538f&utm_medium=social&utm_source=linkedin.com&utm_campaign=buffer, (2015).
Definition of "N(6)-Carboxymethyllysine", printed from Wikipedia, the free encyclopedia on Dec. 8, 2013, 1 page, found at http://en.wikipedia.org/wiki/N(6)-Carboxymethyllysine.
Definition of "Lysine", printed from Wikipedia, the free encyclopedia on Dec. 8, 2013, 1 page, found at http://en.wikipedia.org/wiki/Lysine.
Jarvis, L.M., "Rethinking antibody-drug conjugates", Chemical & Engineering News, vol. 90, issue 25, pp. 12-18, (2012).
Mullin, R., "Cell-free approach to antibody-drug conjugates", Chemical & Engineering News, vol. 91, issue 44, 2 pages, (2013).
Thayer, A.M., "Building antibody-drug conjugates", Chemical & Engineering News, vol. 92, issue 3, pp. 13-21, (2014).
Feige, M.J. et al., "The structural structural analysis of shark IgNAR antibodies reveals evolutionary principles of immunoglobulins", Proceedings of the National Academy of Sciences, vol. 111, No. 22, pp. 8155-8160, (2014).
Philipot, D. et al.,"p16INK4a and its regulator miR-24 link senescence and chondrocyte terminal differentiation-associated matrix remodeling in osteoarthritis", Arthritis Research & Therapy, vol. 16, No. 1, pp. 1-12, (2014).
International Search Report and Written Opinion dated Mar. 31, 2016 for PCT application No. PCT/US2015/050154.
Zhu, Y. et al., "The achilles' heel of senescent cells: from transcriptome to senolytic drugs", Aging Cell, vol. 14, pp. 644-658, (2015).
MX MX/a/2013/013310, mailed Apr. 6, 2016, 7 pages.
CA 2,724,886, mailed Apr. 14, 2016, 5 pages.
AU 2014202548, mailed Apr. 28, 2016, 8 pages.
AU 2014202548, mailed Jun. 20, 2016, 5 pages.
CN 201510303227.8, mailed Jun. 15, 2016, 13 pages.
De Genst, E. et al., "Antibody repertoire development in camelids", Developmental and Comparative Immunology, vol. 30, pp. 187-198, (2006).
Griffin, L.M. et al., "Analysis of hevy and light chain sequences of conventional camelid antibodies from Camelus dromedarius and Camelus bactrianus species", Journal of Immunological Methods, vol. 405, pp. 35-46, (2014).
Hamers-Casterman, C. et al., "Naturally occurring antibodies devoid of light chains", Nature, vol. 363, pp. 446-448, (1993).
Muyldermans, S. et al., "Sequence and structure of $V_H$ domain from naturally occurring camel heavy chain immunoglobulins lacking light chains", Protein Engineering, vol. 7, No. 9, pp. 1129-1135, (1994).
Nguyen, V. K. et al., "Camel heavy-chain antibodies: diverse germline VHH and specific mechanisms enlarge the antigen-binding repertoire", The EMBO Journal, vol. 19, No. 5, pp. 921-930, (2000).
Invitation to Pay Additional Fees and Partial International Search Report dated Jan. 13, 2016 for PCT application No. PCT/US2015/050154.
Feldmann, M. et al., "Anti-TNFalpha therapy of rheumatoid arthritis: What have we learned?", Annual Review of Immunology, vol. 19, pp. 163-196, (2001).
U.S. Appl. No. 12/994,421, mailed Sep. 2, 2015, 4 pages.
MX MX/a/2013/013310, mailed Jul. 27, 2015, 7 pages.
KR 10-2015-7007520, mailed Nov. 27, 2015, 4 pages.
EP 14170802.4, mailed Dec. 10, 2015, 5 pages.
AU 2014202548, mailed Jan. 8, 2016, 3 pages.
AU 2011332143, mailed Jan. 11, 2016, 2 pages.
JP 2015-076575, mailed Jan. 12, 2016, 7 pages.
U.S. Appl. No. 12/994,421, mailed Jan. 19, 2016, 35 pages.
AU 2011332143, mailed Jan. 25, 2016, 2 pages.
WO PCT/US2015/050154, mailed Mar. 31, 2016, 17 pages.
Yuan, Y. et al., "Advanced glycation end products (AGEs) increase human mesangial foam cell formation by increasing Golgi SCAP glycosylation in vitro", American Journal of Physiology—Renal Physiology, vol. 301.1, pp. F236-F243, (2011).
CA 2,818,647, mailed Oct. 26, 2016, 5 pages.
U.S. Appl. No. 14/974,095, mailed Sep. 22, 2016, 6 pages.
Liu, H. et al., "Abstract 154: Vaccination using advanced glycation end product of low-density lipoprotein pulsed dendritic cells reduces atherosclerosis in diabetic apoe-/- mice", Arteriosclerosis, Thrombosis, and Vascular Biology, pp. 1-4, (2012).
Mashitah, M.W. et al., "Immunization of AGE-modified albumin inhibits diabetic nephropathy progression in diabetic mice", Diabetes, Metabolic Syndrome and Obesity: Targets and Therapy, vol. 8, pp. 347-355, (2015).
Sayej, W.N. et al., "Advanced glycation end products induce obesity and hepatosteatosis in CD-1 wild-type mice", BioMed Research International, vol. 6, No. 39, pp. 1-12, (2016).
Srikanth, V. et al., "Advanced glycation endproducts and their receptor Rage in alzheimer's disease", Neurobiology of Aging, vol. 32, No. 5, pp. 763-777, (2011).
International Search Report and Written Opinion dated Dec. 2, 2016 for PCT application No. PCT/US2016/039076.

(56) References Cited

OTHER PUBLICATIONS

Fu, M-X. et al., "The advanced glycation end product, N-(Carboxymethyl)lysine, is a product of both lipid peroxidation and glycoxidation reactions", the Journal of Biological Chemistry, vol. 271, No. 17, pp. 9982-9986, (1996).

Jorgensen, L. et al., "The relationship between atherosclerosis of the thoracic aorta and renal scarring in an autopsy material", Acta Pathol Microbiol Immunol Scand A., vol. 93, No. 5, pp. 251-255, (1985) Abstract Only.

"Senescent cells drive plaque formation in animal models of atherosclerosis, research shows", Mayo Clinic, pp. 1-2, (2016), found at www.news-medical.net/news/20161027/Senescent-cells-drive-plaqueformation-in-animal-models-of-atherosclerosis-research-shows.aspx.

Arichika, S. et al., "Correlation of retinal arterial wall thickness with atherosclerosis predictors in type 2 diabetes without clinical retinopathy", British Journal of Ophthalmology, vol. 101, pp. 69-74, (2017).

Lin, Z. et al., "Vaccination against AGE-LDL significant attenuates atherosclerosis in diabetic apoe mice", Heart, vol. 97, No. 21, supplement 3, p. A18, (2011) Abstract Only.

U.S. Appl. No. 14/932,200, filed Nov. 4, 2015.
U.S. Appl. No. 14/920,737, filed Oct. 22, 2015.
U.S. Appl. No. 14/974,561, filed Dec. 18, 2015.
U.S. Appl. No. 14/974,095, filed Dec. 18, 2015.
U.S. Appl. No. 12/994,421, filed May 22, 2009.
U.S. Appl. No. 12/951,768, filed Nov. 22, 2010.
U.S. Appl. No. 13/332,976, filed Dec. 21, 2011.

Glenn, J.V. et al., "The role of advanced glycation end products in retinal ageing and disease", Biochimica Et Biophysica Acta, vol. 1790, No. 10. pp. 1109-1116, (2009).

European Search Report dated Feb. 21, 2017 for EP application No. 16198527.0.

Peppa, M. et al., "The role of advanced glycation end products in the development of atherosclerosis", Current Diabetes Reports, vol. 4, pp. 31-36, (2004).

\* cited by examiner

SELECTIVE REMOVAL OF AGE-MODIFIED CELLS FOR TREATMENT OF ATHEROSCLEROSIS

CROSS REFERENCE TO RELATED APPLICATION

This application claims priority to provisional application No. 61/386,932 entitled "SELECTIVE REMOVAL OF AGE-MODIFIED CELLS FOR TREATMENT OF ATHEROSCLEROSIS" filed 27 Sep. 2010, the entire contents of which are hereby incorporated by reference, except where inconsistent with the present application.

BACKGROUND

Aging cells undergo several modifications associated with diseased conditions. Hyperglycemia, caused by diabetes mellitus (DM), and oxidative stress promote post-translational modifications of membrane proteins of cells by advanced glycation end-products (AGE). Lindsey J B, et al., "Receptor For Advanced Glycation End-Products (RAGE) and soluble RAGE (sRAGE): Cardiovascular Implications," *Diabetes Vascular Disease Research*, Vol. 6(1), 7-14, (2009) at p. 8. AGE arise from a nonenzymatic reaction of sugars with protein side-chains in aging cells and is involved in the pathogenesis of several age-related disease processes, including adverse complications of diabetes. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999) at p. 123.

AGE-modified erythrocytes have less flexibility than non-modified erythrocytes, and have been implicated in the pathogenesis of atherosclerosis, while the absence of AGE-modified erythrocytes has been correlated with reduced atherosclerosis. Jandeleit-Dahm K, et al., "The AGE/RAGE Axis in Diabetes-Accelerated Atherosclerosis," *Clinical and Experimental Pharmacology and Physiology*, Vol. 35, 329-334 (2008) at 330. Localization of AGEs in atherosclerotic lesions of the aorta in non-diabetic patients has been reported in intima cells, endothelial cells, smooth muscle cells, macrophages and foam cells. Sakata N. et al., "Immunohistochemical Localization of Different Epitopes of Advanced Glycation End Products in Human Atherosclerotic Lesions," *Atherosclerosis*, 141, 61-75 (1998) at p. 71. The damage caused by AGE-modified cells may also lead to nephropathy, retinopathy, neuropathy, heart disease, stroke, and peripheral vascular disease. Karachalias N. et al., "Accumulation of Fructosyl-Lysine and Advanced Glycation End Products in the Kidney, Retina and Peripheral Nerve of Streptozotocin-Induced Diabetic Rats." *Biochemical Society Transactions*, 31, 1423-25 (2003) at 1423.

SUMMARY

In a first aspect, the present invention is a method of treating atherosclerosis comprising removing AGE-modified cells from a patient.

In a second aspect, the present invention is a method of removing AGE-modified erythrocytes from blood, comprising damaging or destroying an AGE-modified erythrocyte with ultrasound.

In a third aspect, the present invention is a method of removing AGE-modified cells, comprising binding the AGE-modified cells with an anti-AGE monoclonal antibody.

In a fourth aspect, the present invention is a method of removing AGE-modified cells from atherosclerotic lesions, comprising binding the AGE-modified cells with an anti-AGE monoclonal antibody.

Definitions

The following definitions are included to provide a clear and consistent understanding of the specification and claims.

The term "advanced glycation end-products" refers to the aggregate of glycated proteins on the cell membrane that are formed as the result of the reaction of sugars with protein side chains, and are also referred to as AGE-modified proteins and AGE-modified cells.

DETAILED DESCRIPTION

The present invention makes use of the discovery that enhanced clearance of AGE-modified cells, such as erythrocytes, is beneficial in reducing cardiovascular disease, especially when present as a complication of diabetes, or the pre-diabetic condition referred to as "Syndrome-X". Elevated blood glucose concentrations lead to modifications of protein side chains in cells, including circulating erythrocytes and other cell types. Non-enzymatic glycation of membrane proteins results in the formation of AGE-modified cells, which cause reduced cell deformability that is associated with the formation of atherosclerotic lesions.

The technique for removing AGE-modified erythrocytes from a patient is selected for its ability to detect and selectively remove or destroy AGE-modified cells while avoiding removal or destruction of cells that are not AGE-modified. For example, AGE-modified erythrocytes may be detected due to their increased stiffness and reduced deformability by ultrasound. In an example, ultrasound treatment may be applied at driving frequencies ranging from 1.0 Mhz to 5.0 Mhz, preferably from 3.0 Mhz to 4.0 Mhz. Time of exposure may range from three to sixty minutes daily for up to 20 days.

Additionally, anti-AGE monoclonal antibodies may be used for their ability to selectively bind AGE-modified cells. Anti-AGE monoclonal antibodies bind to AGE-modified cells, such as AGE-modified erythrocytes, to selectively remove the AGE-modified cells from a patient. The blood from the patient may be passed through extracorporeal circulation and AGE-modified erythrocytes are then bound by anti-AGE monoclonal antibodies attached to a solid substrate via their Fc region.

Further, anti-AGE monoclonal antibodies covalently conjugated to a fluorescent marker may be used to label AGE-modified erythrocytes that are then removed from the patient's blood via cell sorting. An anti-AGE monoclonal antibody is injected into the patient to label AGE-modified erythrocytes and, subsequently, the patient's blood is connected to a cell sorter via extracorporeal circulation tubing system. AGE-modified erythrocytes bound to a fluorescent anti-AGE monoclonal antibody are sorted from normal erythrocytes and other blood cell types.

Anti-AGE monoclonal antibodies can be conjugated to an agent that causes the destruction of AGE-modified cells. Such agent can be, but is not limited to a toxin, a cytotoxic agent, magnetic nanoparticles, and magnetic spin-vortex discs.

Moreover, AGE-modified cell types localized in atherosclerotic lesions of the aorta in non-diabetic patients, such as intima cells, endothelial cells, smooth muscle cells, macrophages, and foam cells, may be selectively removed by using anti-AGE monoclonal antibodies conjugated to an agent that causes the destruction of AGE-modified cells. Such agent can be, but is not limited to a toxin, a cytotoxic agent, magnetic nanoparticles, and magnetic spin-vortex discs.

A toxin, such as pore-forming toxins (PFT) (Aroian R. et al., "Pore-Forming Toxins and Cellular Non-Immune Defenses (CNIDs)," *Current Opinion in Microbiology,* 10:57-61 (2007)), conjugated to an anti-AGE monoclonal antibody may be injected into a patient to selectively target and remove AGE-modified cells. The anti-AGE monoclonal antibody recognizes and binds to AGE-modified erythrocytes or AGE-modified cells present in atherosclerotic lesions. Then, the toxin causes pore formation at the cell surface and subsequent cell removal through osmotic lysis (Id. at p. 58).

Magnetic nanoparticles conjugated to anti-AGE monoclonal antibodies may be injected into a patient to target and remove AGE-modified erythrocytes or AGE-modified cells present in atherosclerotic lesions. The magnetic nanoparticles can be heated by applying a magnetic field in order to selectively remove the AGE-modified erythrocytes or AGE-modified cells present in atherosclerotic lesions.

As an alternative, magnetic spin-vortex discs, which are magnetized only when a magnetic field is applied to avoid self-aggregation that can block blood vessels, begin to spin when a magnetic field is applied, causing membrane disruption of target cells. Magnetic spin-vortex discs, conjugated to anti-AGE monoclonal antibodies specifically target AGE-modified cell types, without removing other cells.

EXAMPLES

Example 1 (Prophetic)

Ultrasound Removal of AGE-Modified Erythrocytes in ZDF (Zucker Diabetic Fatty) Rats In this example ZDF rats, a type II diabetic rat model demonstrating obesity, insulin resistance, hyperinsulinemia, hyperglycemia, hypertriglyceridemia, hypercholesterolemia, nephropathy, impaired wound healing, mild hypertension, and neuropathy, are exposed to ultrasound to determine (1) the background level of glycated hemoglobin A1c in this strain; (2) whether exposure to ultrasound at clinical imaging levels, is tolerable by assessing clinical observation on the animals; (3) whether there is an effect on the level of glycated hemoglobin A1c due to exposure to ultrasound. The level of glycated hemoglobin A1c is used as a marker for removal of AGE-modified erythrocytes.

Ten ZDF rats, approximately eight weeks old at receipt, supplied by Charles River Laboratories (Wilmington, Mass.) are randomly assigned in two groups, labeled I and II. The animals are weighed prior to ultrasound exposure. The rats are shaved dorsally and ultrasound gel is applied by pressing and rubbing the applicator across the dorsal aspect of the rat, from thorax from tail. While one technician holds the animal, another uses the applicator. The ultrasound machine is set at 3.3 Mhz and the applicator is pressed against the dorsal aspect of the animal and moved slowly from thorax to tail for the appropriate time of exposure. Rats in group I are exposed to five minutes of ultrasound at 3.3 Mhz/day for ten days and rats in group II are exposed to ten minutes of ultrasound at 3.3 Mhz/day for ten days. Following exposure the animal is wiped off to remove ultrasound gel and placed back in its cage. The animals remain under observation for four hours within four hours from exposure for any clinical evaluation. Blood samples are taken from each animal via retro-orbital bleeding prior to exposure to ultrasound, then at day five, and after the last exposure, at day ten. To analyze the blood samples a (GhbA1c) ELISA kit (Cusabio Biotech Co., Ltd, Japan) is used. All data documenting experimental details and study procedures are recorded and analyzed to assess effect on the levels of glycated hemoglobin A1c.

Example 2 (Prophetic)

Removal of AGE-Modified Erythrocytes by Monoclonal Antibodies

In this example, anti-AGE monoclonal antibody 6D12 (Ando K. et al., supra), or anti-AGE humanized monoclonal antibody is conjugated to a toxin, such as pore-forming toxins or PTFs (Aroian R. et al., Pore-Forming Toxins and Cellular Non-Immune Defenses (CNIDs), *Current Opinion in Microbiology,* 10:57-61 (2007)), magnetic nanoparticles, magnetic spin-vortex discs (Dobson J., "A Twist on Tumour Targeting," *Nature Materials,"* 9, 95-96 (2010)), or a cytotoxic agent, such as selenocystamine, and IP injected in ZDF rats to selectively bind and remove AGE-modified erythrocytes.

ZDF rats are IP injected in the volume of 200 µl for the initial loading dose of 10 mg/kg of the anti-AGE-monoclonal antibody or with 200 µl PBS 1× control. Each rat receives an IP injection per week for a total of six weeks. The animals are weighed weekly and are observed daily for any clinical evaluation. Blood samples are taken from each animal via retro-orbital bleeding every week. The level of glycated hemoglobin A1c is used as a marker for removal of AGE-modified erythrocytes. All data documenting experimental details and study procedures are recorded and analyzed to assess effect on the levels of glycated hemoglobin A1c.

Example 3 (Prophetic)

Removal of AGE-Modified Erythrocytes by Panning Selection

In this example, AGE-modified erythrocytes are isolated from a patient by panning selection, using an anti-AGE monoclonal antibody. Extracorporeal blood purification is utilized to remove AGE-modified cells from a patient.

The patient's blood is passed through an extracorporeal tubing system containing a sorbent agent, i.e. an anti-AGE monoclonal antibody to selectively remove AGE-modified erythrocytes from the blood. Anti-AGE monoclonal antibodies attached to a solid substrate through their Fc region, bind AGE-modified erythrocytes and remove them from the patient's blood. The blood is recirculated through extracorporeal circulation to remove most AGE-modified erythrocytes and the duration of the procedure is performed following standards known in the art for removing other corpuscolated elements from the blood, e.g. platelets. Gutensohn K. et al., "Extracorporeal Plateletpheresis Induces the Interaction of Activated Platelets with White Blood Cells," *Vox Sanguinis*, Vol. 78(2), 101-05 (2000). At the end of the procedure, the patient's intracorporeal circulation is restored.

Alternatively, an anti-AGE monoclonal antibody conjugated to a marker, e.g. a fluorescent marker, is injected into a patient. The patient's blood is passed through an extracorporeal tubing system connected to a cell sorter. AGE-modified erythrocytes bound to anti-AGE monoclonal antibodies are sorted by selecting the fluorescent erythrocytes and therefore removed from the patient's blood. At the end of the procedure, the patient's intracorporeal circulation is restored.

Example 4 (Prophetic)

Removal of AGE-Modified Erythrocytes by Pore-Forming Toxins (PFTs)

In this example, AGE-modified erythrocytes are targeted by anti-AGE monoclonal antibodies conjugated to a pore-forming toxin. Pore-forming toxins cause osmotic lysis in erythrocytes. Pore-forming toxins can be conjugated to monoclonal antibody to specifically target a particular cell type. See for example, U.S. Pat. No. 5,817,771, "Cell Targeted Lytic Pore-Forming Agents."

Anti-AGE monoclonal antibodies conjugated to a pore-forming toxin are injected in a patient. The anti-AGE monoclonal antibodies selectively bind and cause the lysis of AGE-modified erythrocytes via the conjugated pore-forming toxin.

Example 5 (Prophetic)

Removal of AGE-Modified Cells in Atherosclerotic Lesions by Pore-Forming Toxins (PFTs)

In this example, AGE-modified cells in atherosclerotic lesions are targeted by anti-AGE monoclonal antibody 6D12 (Ando K. et al., supra), or anti-AGE humanized monoclonal antibody conjugated to a toxin, such as pore-forming toxins or PTFs (Aroian R. et al., supra). Pore-forming toxins cause osmotic lysis in AGE-modified cells. Pore-forming toxins can be conjugated to monoclonal antibody to specifically target a particular cell type. See for example, U.S. Pat. No. 5,817,771, "Cell Targeted Lytic Pore-Forming Agents."

Anti-AGE monoclonal antibodies conjugated to a pore-forming toxin are injected in a patient. The anti-AGE monoclonal antibodies selectively bind and cause the lysis of AGE-modified cells in atherosclerotic lesions, such as intima cells, endothelial cells, smooth muscle cells, macrophages, and foam cells, via the conjugated pore-forming toxin.

REFERENCES

1. Lindsey J B, et al., "Receptor for Advanced Glycation End-Products (RAGE) and soluble RAGE (sRAGE): Cardiovascular Implications," *Diabetes Vascular Disease Research*, Vol. 6(1), 7-14, (2009).

2. Ando K, et al., "Membrane Proteins of Human Erythrocytes Are Modified by Advanced Glycation End Products During Aging in the Circulation," *Biochemical and Biophysical Research Communications*, Vol. 258, 123-27 (1999).

3. Jandeleit-Dahm K, et al., "The AGE/RAGE Axis in Diabetes-Accelerated Atherosclerosis," *Clinical and Experimental Pharmacology and Physiology*, Vol. 35, 329-334 (2008).

4. Sakata N. et al., "Immunohistochemical Localization of Different Epitopes of Advanced Glycation End Products in Human Atherosclerotic Lesions," *Atherosclerosis*, 141, 61-75 (1998).

5. Karachalias N. et al., "Accumulation of Fructosyl-Lysine and Advanced Glycation End Products in the Kidney, Retina and Peripheral Nerve of Streptozotocin-Induced Diabetic Rats." *Biochemical Society Transactions*, 31, 1423-25 (2003).

6. Aroian R. et al., Pore-Forming Toxins and Cellular Non-Immune Defenses (CNIDs), *Current Opinion in Microbiology*, 10:57-61 (2007).

7. Dobson J., "A Twist on Tumour Targeting," *Nature Materials,"* 9, 95-96 (2010).

What is claimed is:

1. An anti-AGE humanized monoclonal antibody for the treatment of atherosclerosis, wherein the anti-AGE humanized monoclonal antibody is conjugated to at least one agent selected from the group consisting of a toxin or a cytotoxic agent, magnetic nanoparticles, and magnetic spin-vortex discs.

2. The anti-AGE humanized monoclonal antibody of claim 1, wherein the antibody is conjugated to a toxin.

3. The anti-AGE humanized monoclonal antibody of claim 2, wherein the toxin is a pore-forming toxin (PFT).

4. The anti-AGE humanized monoclonal antibody of claim 1, wherein the antibody is conjugated to a cytotoxic agent.

5. The anti-AGE humanized monoclonal antibody of claim 4, wherein the cytotoxic agent is selenocystamine.

6. The anti-AGE humanized monoclonal antibody of claim 1, wherein the antibody is conjugated to a magnetic nanoparticle.

7. The anti-AGE humanized monoclonal antibody of claim 1, wherein the antibody is conjugated to a magnetic spin-vortex disc.

8. A pharmaceutical composition for the treatment of atherosclerosis comprising:
   an effective amount of an anti-AGE humanized monoclonal antibody, and
   at least one pharmaceutically acceptable excipient,
   wherein the anti-AGE humanized monoclonal antibody is conjugated to at least one agent selected from the group consisting of a toxin or a cytotoxic agent, magnetic nanoparticles, and magnetic spin-vortex discs.

9. The pharmaceutical composition of claim 8, wherein the pharmaceutically acceptable excipient comprises a diluent, adjuvant or carrier.

10. A method of treating atherosclerosis comprising: removing AGE-modified cells from a patient, wherein the AGE-modified cells are removed by binding with an anti-AGE monoclonal antibody.

11. The method of claim 10, wherein the AGE-modified cells comprise at lease one cell type selected from the group consisting of intima cells, endothelial cells, smooth muscle cells, macrophages, and foam cells.

12. The method of claim 10, wherein the patient is a mammal.

13. The method of claim 10, wherein the patient is a human.

14. The method of claim 10, wherein the patient has Syndrome-X.

15. The method of claim 10, wherein the anti-AGE monoclonal antibody is conjugated to at least one agent selected from the group consisting of a toxin or cytotoxic agent, magnetic nanoparticles, and magnetic spin-vortex discs.

16. The method of claim 10, wherein the AGE-modified cells comprise intima cells.

17. The method of claim 10, wherein the AGE-modified cells comprise endothelial cells.

18. The method of claim 10, wherein the AGE-modified cells comprise smooth muscle cells.

19. The method of claim 10, wherein the AGE-modified cells comprise macrophages.

20. The method of claim 10, wherein the AGE-modified cells comprise foam cells.

* * * * *

UNITED STATES PATENT AND TRADEMARK OFFICE
CERTIFICATE OF CORRECTION

PATENT NO. : 9,649,376 B2
APPLICATION NO. : 13/876157
DATED : May 16, 2017
INVENTOR(S) : Lewis Gruber It is certified that error appears in the above-identified patent and that said Letters Patent is hereby corrected as shown below:

In the Claims

Column 6, Line 48, please delete "lease" and insert --least--

Signed and Sealed this
Seventeenth Day of April, 2018

Andrei Iancu
*Director of the United States Patent and Trademark Office*